(12) United States Patent
Callegaro et al.

(10) Patent No.: US 8,263,118 B2
(45) Date of Patent: Sep. 11, 2012

(54) BIORESORBABLE FILLERS CONSTITUTED BY PHOSPHOLIPID LIPOSOMES AND HYALURONIC ACID AND/OR THE DERIVATIVES THEREOF

(75) Inventors: Lanfranco Callegaro, Abano Terme (IT); Devis Galesso, Abano Terme (IT); Anna Taglienti, Rome (IT)

(73) Assignee: Fidia Farmaceutici S.p.A., Abano Terme (IT)

( * ) Notice: Subject to any disclaimer, the term of this patent is extended or adjusted under 35 U.S.C. 154(b) by 0 days.

(21) Appl. No.: 13/397,646

(22) Filed: Feb. 15, 2012

(65) Prior Publication Data

US 2012/0148667 A1 Jun. 14, 2012

Related U.S. Application Data

(62) Division of application No. 11/920,009, filed as application No. PCT/EP2006/003898 on Apr. 21, 2006, now abandoned.

(51) Int. Cl.
| | |
|---|---|
| *A61K 9/127* | (2006.01) |
| *A61K 38/39* | (2006.01) |
| *A61P 17/00* | (2006.01) |
| *A61P 19/02* | (2006.01) |
| *A61P 29/00* | (2006.01) |
| *A61P 19/00* | (2006.01) |

(52) U.S. Cl. ...... 424/450; 514/18.6; 514/16.6; 514/17.1
(58) Field of Classification Search .................. None
See application file for complete search history.

(56) References Cited

U.S. PATENT DOCUMENTS

| | | | |
|---|---|---|---|
| 5,942,245 A | 8/1999 | Katinger et al. | |
| 6,444,791 B1 | 9/2002 | Quay | |
| 7,836,256 B2 | 11/2010 | Kailas et al. | |
| 2004/0013627 A1 | 1/2004 | Hirai et al. | |

FOREIGN PATENT DOCUMENTS

| | | |
|---|---|---|
| DE | 4322158 A1 | 1/1995 |
| EP | 0295092 A2 | 12/1988 |
| WO | WO-03000190 A2 | 1/2003 |
| WO | WO-2004004671 A1 | 1/2004 |

OTHER PUBLICATIONS

International Search Report, Aug. 9, 2006.
Sezer et al. (2004) Journal of Lipid Research: 14(1-2); 77-86 (Abstract Only).

*Primary Examiner* — Robert M Kelly
(74) *Attorney, Agent, or Firm* — Birch, Stewart, Kolasch & Birch, LLP

(57) ABSTRACT

The present invention describes a new bioresorbable filler constituted by hyaluronic acid and/or the derivatives thereof structured with/in phospholipid liposomes, which increase the residence time of the starting polymer in situ. Said fillers described herein are substantially intended to increase the soft tissues in aesthetic surgery and dermocosmetics for the correction of mild to medium defects, but because of their special characteristics they can also be used in other fields of application.

15 Claims, No Drawings

BIORESORBABLE FILLERS CONSTITUTED BY PHOSPHOLIPID LIPOSOMES AND HYALURONIC ACID AND/OR THE DERIVATIVES THEREOF

This application is a Divisional of co-pending application Ser. No. 11/920,009 filed on Dec. 4, 2007, and for which priority is claimed under 35 U.S.C. §120. application Ser. No. 11/920,009 is the national phase of PCT International Application No. PCT/EP2006/003898 filed on Apr. 21, 2006 under 35 U.S.C. §371 and claims priority to Application No. PD2005A000146 filed in Italy on May 20, 2005; the entire contents of all are hereby incorporated by reference.

SUBJECT OF THE INVENTION

The present invention describes and claims a new bioresorbable filler constituted by hyaluronic acid and/or the derivatives thereof structured with/in phospholipid liposomes, which increase the residence time of the starting polymer in situ. The fillers described herein are substantially intended to increase the soft tissues in aesthetic surgery and dermocosmetics for the correction of mild to medium defects, but because of their special characteristics they can also be used in other fields of application.

BACKGROUND OF THE INVENTION

Filling out the soft tissues is performed in plastic surgery to correct skin defects such as wrinkles, facial grooves and pitting. It can also increase the volume of particular areas such as deep scars, the lips and cheekbones, and better define the facial features and shape. These results are obtained by injecting fillers into the superficial or deep dermis to swell the area to be treated, making it firmer. Besides filling the depression, the injection triggers a phase of biostimulation of the skin cells, so that the skin itself looks healthier, firmer and rosier.

The substances used are called fillers and they are many and various. They can be substantially differentiated into three different types:
  bioresorbable fillers; biocompatible substances that are subject to gradual and ultimately complete resorption by the organism. The most commonly used are collagen (Zyderm®, Zyplast®) and hyaluronic acid (Hylaform®, Ial System®, Restylane®) which give good results, especially in the correction of mild to medium defects, which are the most commonly treated. These materials are however limited because they may prove allergenic (especially collagen), in the presence of contaminating biological material (such as viruses or protein residues) due to the extraction process, and, more importantly, they require frequent administration in order to maintain their effect. Indeed, these are substances, hyaluronic acid in particular, that are rapidly degraded both by the enzymes and the free radicals that are physiologically present in the dermis. The resulting turgor can only be maintained by frequent booster injections of the product, with a consequent increase in the risk of side effects and discomfort to the patient;
  Semi-permanent fillers, that last longer once they have been implanted in the tissues, as they are constituted by a bioresorbable matrix which incorporates particles such as polymethacrylate or acrylic hydrogel or dextran (among the commercial products of this kind are Artecoll®, Dermalive® and Reviderm® Intra). After resorption of the matrices, the non-biodegradable particles do maintain a certain degree of turgor but they may also cause inflammatory phenomena and marked allergic reactions;
  permanent fillers, that are not resorbed by the organism. The products are based on hydrogels of polyacrylamide, Gore-Tex® or other completely synthetic materials which, after implantation, become progressively surrounded by a capsule of connective tissue that fixes them firmly in place. If on the one hand this is an advantage, because it renders the implant permanent, on the other it makes it difficult, but theoretically not impossible, to alter the effect or remove the implant if the desired effect is not achieved. Implanting permanent fillers is a surgical procedure, so the risks and benefits must be weighed up, creating a further limitation.

The choice of filler is based on a series of parameters such as the desired effect and its duration, biocompatibility, painfulness, the possible need for allergy tests beforehand and the cost. In the field of bioresorbable fillers, one of the key factors when choosing is certainly the duration of the implant. Indeed, it is essential to choose a product that not only has all the aforesaid properties but also stays at the injection site for a long time, so as to reduce the number of administrations necessary to maintain the effect. This translates into a lesser risk of side effects due to the injection procedure (e.g. swelling, intumescence, burning) and consequently less discomfort for the patient. The limitations of the current state of the art have been overcome by the present invention, which describes and claims a bioresorbable filler based on hyaluronic acid and/or the derivatives thereof, structured with/in phospholipid liposomes that increase their residence time and improve their overall performance.

Hyaluronic acid (HA) is a well-known molecule: it is a heteropolysaccharide constituted by D-glucuronic acid and N-acetyl-glucosamine, and is present in practically every compartment of our organism. HA plays numerous physiological roles, ranging from mechanical support for the cells of many tissues to joint lubrication, the modulation of many biological and physiological processes (including cell proliferation, migration and differentiation, mediated by the interaction with its membrane receptor, CD44). HA's protective effect against the degeneration of cartilage that has been damaged by disease or trauma is well known. In such situations there is a strong concentration of pro-inflammatory cytokines in the joint cavity, especially interleukine-1 (IL-1), that promote cartilage disintegration and inhibit chondrocyte proliferation (van Beuningen H. M. et al., *Arthritis Rheum*, 1991, 34:606-615). Various scientific experiments have demonstrated that hyaluronic acid is able to oppose the action of IL-1, drastically reducing its negative effects and then exercising a reparatory effect on the cartilage tissue in the joint into which it has been injected. (Stove J. et al., *J Orthop Res*, 2002, 20:551-555). In the joints, the hyaluronic acid content in the synovial fluid acts as a viscous lubricant during slow movement, while during brisk movement its elastic properties absorb any trauma or microtrauma that may affect the joint. In pathological situations, both the concentration and mean molecular weight of HA (Balazs E A. et al., J Rheumatol Suppl, 1993, 12:75-82; Belcher C. et al., Annals of the Rheumatic Disease, 1997, 56:299-307) decrease considerably, altering the physiological features of the synovial fluid.

Its tissue-hydrating and wound-healing properties are also widely known and have long been put to use in medications for the treatment of wounds, ulcers and skin lesions of various origin (e.g., Balasz A. et al., *Cosmetics & Toiletries*, 1984, 5:8-17).

Numerous chemical modifications that can be performed on the HA molecule are also known to the state of the art, that is:

salification with organic and/or inorganic bases (EP 138572 B1);

esterification of HA with alcohols of the aliphatic, araliphatic, cycloaliphatic, aromatic, cyclic and heterocyclic series (HYAFF®), with a percentage of esterification that may vary according to the type and length of the alcohol that is used (EP 216453 B1);

amidation of HA with amines of the aliphatic, araliphatic, cycloaliphatic, aromatic, cyclic and heterocyclic series (HYADD™), with a percentage of amidation ranging between 0.1 and 50% (EP 1095064 B1);

O-sulphatation of HA to the 4th degree of sulphatation (EP 702699 B1);

Inner esterification of HA with a percentage of esterification not exceeding 20% (ACP®; EP 341745 B1); deacetylation of HA: the N-acetyl-glucosamine fraction is deacetylated, preferably to a percentage of between 0.1 and 30% (EP 1313772 B1);

percarboxylation of HA achieved by oxidising the primary hydroxyl of the N-acetyl-glucosamine fraction to a degree of percarboxylation of between 0.1 and 100% (HYOXX™; patent application EP 1339753).

The polymers obtained by these processes maintain the characteristics of biodegradability, biocompatibility, and easy handling and use of the starting polysaccharide, but they give a better mechanical performance.

The hyaluronic acid used in the present invention may derive from any source. For example, it may be extracted from rooster combs (EP 138572 B1) or obtained by fermentation (EP 716688 B1) or by technological means, and its molecular weight may range between 50,000 and 3,000,000 Da.

The type of technical solution described and claimed in the present invention is, however, absolutely innovative, and the fillers of HA and/or the derivatives thereof therefore remain at the application site for a long time, significantly reducing the need for frequent administrations while maintaining the characteristics of biocompatibility, safety and easy handling and use of the starting polysaccharide. This characteristic is achieved by structuring the hyaluronic acid and/or the derivatives thereof with/in phospholipid liposomes, as illustrated hereafter. Liposomes are hollow microspheres of varying size, ranging between 50 nm and 1000 nm, formed by one or more double lipid layers that enclose a hydrophilic core. This structure can be achieved thanks to the special nature of phospholipids that have a hydrophobic tail and hydrophilic head; in an aqueous medium the hydrophobic tails attract one another while the hydrophilic heads tend to face water. The result is double lipid layers that close to form small vesicles inside which there is a variously hydrophilic environment. Liposomes were first described in 1965 (Standish MM et al., *J Mol Biol,* 1965, 13:238-252) and have been researched as carriers for drugs and/or active ingredients (e.g., *Liposomes as drug carriers,* Gregoriadis G. editor, New York: John Wiley & Sons, 1985: 3-18; Banerjee R., *J Biomater Appl,* 2001, 16:3-21). They are normally classified on the basis of their size and the number of double lipid layers. Generally speaking, as described, for example, by Callow R A et al. (*Cryobiology,* 1985:251-267), reference is made to multilamellar vesicles: they have an onion-like structure wherein a number of double lipid layers are interspersed with hydrophilic layers;

unilamellar vesicles, large (diameter of over 1 μm) and small (diameter of less than 1 μm): they are formed by one single double lipid layer and enclose a strongly hydrophilic nucleus;

oligolamellar vesicles, constituted by several double lipid layers that enclose a markedly hydrophobic environment.

Further classifications are possible on the basis of numerous processes by which liposomes can be obtained and which are well known to the expert in the field. Combinations of HA and phospholipids have already been described both as simple physical mixtures (WO 91/12026) and as proper chemical associations (EP 581282 B1) intended for use as antirheumatic drugs for intra-articular use, for which the lubricating properties of both liposomes and the polysaccharides in question are claimed. Also known is patent application EP 1406571 that describes and claims the use of glycosaminoglycans encapsulated in phospholipid liposomes for the intra-articular treatment of osteoarthrosis.

The Applicant intends to demonstrate hereafter that the present invention differs substantially from those already known in the type of polysaccharide used and also in the way in which it is structured.

DETAILED DESCRIPTION OF THE INVENTION

The present invention describes and claims a new bioresorbable filler constituted by hyaluronic acid and/or the derivatives thereof structured with/in phospholipid liposomes, to be used substantially to fill the soft tissues, for aesthetic and/or dermocosmetic purposes. This type of solution enables an increase in the filler's residence time at the injection site, thus reducing the need for repeated and frequent administrations and, consequently, markedly reducing the risk of unwanted side effects and discomfort to the patient. The association of HA-liposomes is achieved, as described hereafter, by treating a film of phospholipid liposomes with a solution of HA and/or the derivatives thereof so that part of the polysaccharide is incorporated in the liposomes and part remains outside, enveloping the phospholipid structures. A sort of macrostructure is thus created that ensures immediate firmness to the treated area and also proves more resistant to the enzymatic and chemical degradation that the polysaccharide undergoes after administration. For the sake of simplicity, the above will be defined in the present invention as "structuring HA and/or the derivatives thereof with/in liposomes".

Therefore it is object of the present invention hyaluronic acid and/or a derivative thereof structured with/in liposomes as a soft tissue filler and/or for the correction of skin defects.

Preferably, the molecular weight of the hyaluronic acid ranges between 50,000 and $3 \times 10^6$ Da.

Hyaluronic acid and/or a derivative thereof structured with/in liposomes according to the present invention can be hyaluronic acid derivatives chosen from a group including salts, esters, inner esters, amides 0-sulphatated derivatives, percarboxylated derivatives. Preferably the hyaluronic acid derivative is a hexadecyl amide.

In particular, the concentration of hyaluronic acid and/or of the derivative thereof ranges between 0.1 and 50 mg/ml. Hyaluronic acid and/or a derivative thereof structured with/in liposomes constituted by phospholipids. Preferably the phospholipid is dipalmitoyl phosphatidylcholine. The concentration of phospholipid preferably ranges between 0.1 and 50 mg/ml and more preferably the concentration of phospholipid is equal to 5 mg/ml.

It is a further object of the present invention a pharmaceutical composition containing hyaluronic acid and/or a derivative thereof structured with/in liposomes as a soft tissue filler and/or for the correction of skin defects and/or for the integration/substitution of the synovial fluid in intra-articular treatment of osteoarthrosis.

In particular said pharmaceutical composition according to the present invention contains pharmacologically and/or biologically active substances.

In pharmaceutical compositions for the integration/substitution of the synovial fluid in intra-articular treatment of osteoarthrosis, the hyaluronic acid derivative is preferably the methylprednisolone ester. More preferably the hyaluronic acid is esterified to a degree of 45% with 6α-methylprednisolone.

It is also object of the present invention the use of the pharmaceutical composition containing hyaluronic acid and/or a derivative thereof structured with/in liposomes for the correction of skin defects and/or as a soft tissue filler and/or as an integrator/substitute for the synovial fluid in the intra-articular treatment of osteoarthrotic pathologies.

Besides hyaluronic acid as such, its derivatives have also been used, obtained from chemical modification by salification, partial and/or total esterification, inner esterification, deacetylation, O-sulphatation, percarboxylation and amidation. Particularly suitable for the purposes specified herein have proved the amide derivatives of HA, in which the hyaluronic acid is linked with amines of the aliphatic, araliphatic, cycloaliphatic, aromatic, cyclic and heterocyclic series, with a percentage of amidation of between 0.1 and 50%, while the remaining percentage of HA that has not been amidated may possibly be salified with organic and/or inorganic bases. The derivatives thus obtained (HYADD™) maintain the characteristics of biocompatibility and biodegradability of the starting molecule, but they give a better mechanical performance. As regards liposomes, among the various preparation procedures known to the state of the art, we have chosen to use the classic lipid film technique for the production of unilamellar liposomes: the lipids selected that will constitute the double layer are mixed with an organic solvent and then exposed to set environmental conditions (for example, set parameters of pressure and temperature) so as to allow the solvent to evaporate and the dry lipid film to form. The lipid film is then hydrated with an aqueous medium and/or with the solution containing the polymer to be associated with the liposomes. One part of the mixture is frozen, freeze-dried and then reconstituted to its initial volume by adding a suitable medium. The step of freezing, freeze-drying and reconstituting was devised on the basis of experimental findings (Peer at al., *Biochim Biophys Acta*, 2003, 1612:76-82) demonstrating that hyaluronic acid and/or the derivatives thereof can act as cryoprotectors for the unilamellar liposome microstructures. Generally, when simple, structured-phospholipid suspensions are freeze-dried and then reconstituted, the liposomes lose their original characteristics, and become organised in far larger multilamellar vesicles, that are unsuitable for the purposes of the present invention because their structure and the controlled release of the material they are carrying are ineffective. The presence in the mixture to be freeze-dried of significant quantities of polysaccharides conserves the original structural properties of the liposomes by the formation of stabilising hydrogen bonds and maintains their efficacy as controlled release systems following their reconstitution. In the case of hyaluronic acid and/or the partially substituted derivatives thereof, especially its high-molecular-weight fractions, the stabilising effect seems to be accompanied by a global structural organisation where a considerable part of the polysaccharide contained in the formulate covers the outer, hydrophilic surface of the double phospholipid layer and forms a bridge between two or more liposomes. In the places where the hyaluronic acid spreads from one liposome to another, tubular structures can be seen under a microscope. In this situation, the polysaccharide chain is wrapped in a sheath formed by a double phospholipid layer hooked to it by hydrogen bonds.

A process of this kind for structuring the polysaccharide with/in liposomes is therefore substantially different from the one described in the state of the art and results in a product that immediately has a firming effect on the treated area that lasts for a long time, especially on account of the prolonged protection that is exercised by the liposomes on the polysaccharide chain. The presence in situ of the preparation for such a long time also enables the HA to continue to produce its beneficial effects of cell stimulation and proliferation mediated by the action on the CD44 receptor, discussed earlier, thereby ensuring not only a filling effect but also a biological effect of stimulation and revitalisation of the dermis. The hyaluronic acid that is used is very similar to that which is physiologically present in our organism and does not even require allergy tests to be performed before being applied.

The liposomes are formed by a lipid constituted by a hydrophilic part and a lipophilic part that may have a single or multiple, saturated or unsaturated, linear or branched chain, of natural or synthetic origin.

Other elements may be added, such as cholesterol, which stabilise the liposomes in the biological fluids, or any other element known to the expert in the field to have the desired effect.

In the case in point, the most commonly used substances are those with two or more lateral lipophilic chains. For purely illustrative purposes, and without being limited by the same, we can mention those of the lipophilic cationic chains that contain two saturated and/or unsaturated fatty acids with, for example, between 10 and 30 carbon atoms, the salts of fatty acids with quaternary amines, quaternary dimethyldiacylamines where the acyl groups contain between 8 and 30 carbon atoms. Further examples are amply described in the literature (including Fasbender et al., *Am J Physiol*, 1995, 269:L45-L51; Solodin et al, *Biochemistry*, 1995, 34:13537-13544; Feigner et al., *J Biol Chem*, 1994, 269:2550-2561; Stamatatos et al., *Biochemistry*, 1988, 27:3917-3925).

Of the non-ionic chains, we can mention glyceric diesters with for example between 10 and 30 carbon atoms, and alkoxylated amines, examples of anionic lateral chains including phosphatidic acids and negatively charged phospholipids such as dipalmitoylphosphatidylglycerol. Examples of substances with a single, non-ionic chain are monoglyceric esters with between 10 and 30 carbon atoms in the chain, such as glyceryl caprate, caprylate, hydroxystearate, lysostearate, lanolate, laurate, linolate, etc.

Liposomes may also be constituted by polyoxyethylene derivatives to which lipophilc chains are bound by ether and/or ester bonds. For illustrative purposes we can mention cetyl and stearic ethers, and all those with between 3 and 10 oxyethylene units, and the derivatives thereof.

The substances with a single anionic chain include, but are not limited to, fatty acids such as oleic acid and negatively charged phospholipids with a single chain such as phosphatidylserine and phosphatidylglycerol.

Lastly, the liposome may be constituted by phospholipids of either natural or synthetic origin. Natural phospholipids include egg phosphatidylcholine, as such or hydrogenated, and phospholipids from soya or other vegetal sources.

Synthetic phospholipids include dilauroylglycerophosphocholine (DLPC), dimiristoylglycerophosphocholine (DSPC), palmitoyloleoylglycerophospho-choline (POPC), phosphatidylethanolamine, dipalmitoylphosphatidylglycerol (DPPG), dipalmitoylphosphatidylcholine (DPPC), dipalmitoylphosphatidic acid (DPPA), phosphatidylserine and any possible derivative thereof. Clearly, there are a multitude of possible combinations that can be made to obtain liposomes that are suitable for the purpose and, since they have already been amply reported in the literature, a technical expert in the field will be able to choose the most suitable.

According to the present description and claims, the structuring of hyaluronic acid and/or the derivatives thereof with/in liposomes makes the polysaccharide less open to attack by free radicals and less prone to enzymatic catabolism of hyaluronidase. This conclusion was reached after specific testing of various preparations of HA and/or derivatives thereof structured with/in liposomes. The various formulations prepared on each occasion were characterised by advanced spectroscopic and microscopic techniques, so as to obtain valuable structural information on the various mechanical and biological behaviours. Rheological and spectroscopic determinations were performed on various formulations in which the lipid component had been varied so as to modulate the chemical-physical characteristics of the liposomes obtained. The concentration of the chosen phospholipid varied between 0.1 and 50 mg/ml, preferably between 0.5 and 10 mg/ml and most preferably at 5 mg/ml. As regards the polysaccharide, we used concentrations of HA and/or the derivative thereof that ranged between 0.1 and 50 mg/ml, preferably between 5 and 15 mg/ml and more preferably still around 10 mg/ml.

The tests assessed resistance to degradation by free radicals and enzymes and resistance time in vitro.

In the enzymatic resistance tests the various preparations were exposed to the action of the $Cu^{2+}$/ascorbate system, which can produce OH radicals (mimicking the condition of inflamed tissue), and viscosimetric measurements were made in terms of time. Generally speaking, starting with formulations of hyaluronic acid and/or a derivative thereof, either structured with/in liposomes or free in solution, with similar basic viscosity, the former presented significantly more consistent viscosity maintenance. When exposed to enzymatic attack by bovine hyaluronidase, the same formulations generally confirmed the above. The formulations of HA and/or derivatives structured with/in liposomes did indeed undergo a minor decrease in dynamic viscosity compared to the corresponding formulations of HA and/or free derivatives in solution. All this explains the increased residence time in situ and therefore the prolonged firming effect observed with the subcutaneous implant described and claimed herein.

Studies on the residence time have also been performed on a model in vivo: suitable formulations of HA and/or derivatives prepared according to the present invention and free in solution have been administered into rabbit joints. This site was chosen because of the abundant concentration of hyaluronidase in the synovial fluid. The preparations were thus exposed to an extreme situation, in terms of degradation of the polysaccharide part. In the case of the liposome formulation the results showed a peak exogenous HA concentration 1 day after administration, a return to baseline values 3 days later and an increase in values on the 7th and 14th days, showing a constant trend, typical of a release system. Conversely, the preparations containing HA and/or free derivatives in solution were progressively and rapidly consumed by the enzyme, leading in a short time to the elimination of the exogenous surplus.

From an analysis of the results, it can be seen that the liposome structures enable the product to remain in situ thanks to a combination of effects, namely a mechanical-type action: the macrostructure that is formed consistently slows down the catabolic action of the enzymes and free radicals that begin to be active immediately the product is administered a shielding action: the liposomes become the target of the circulating free radicals and before the polysaccharide part inside the liposomes can also be degraded by hyaluronidase, the liposomes themselves must be destroyed.

prolonged presence of HA and/or the derivatives thereof in the implantation site; the existence of HA and/or the derivatives thereof outside and inside the liposomes enables a protracted interaction with the CD44 receptor and therefore a more consistent stimulating activity on the migration and proliferation of the fibroblasts that constitute the dermis. This contributes towards significantly improving the appearance of the treated area, which appears rosier, smoother and revitalised.

The aforesaid therefore demonstrates that a bioresorbable filler constituted by HA and/or a derivative thereof structured with/in phospholipid liposomes so that the polysaccharide is to be found both inside and outside the liposomes enables an immediate manifestation of firmness and of the effect of cellular stimulation, thanks to the polysaccharide outside the liposomes prolonged residence in situ after subcutaneous injection of the product and thus overcomes the limitations of the current state of the art in the field of corrective surgery and dermocosmetics for skin defects by means of fillers for the soft tissues.

The results obtained in rabbit joint, moreover, suggest a further important application for the product that is the subject of the present invention. Indeed, if the polysaccharide is a medium—(between 500,000 and 750,000 Da) or high-molecular-weight (over 1,500,000 Da) hyaluronic acid or a derivative thereof, preferably a partial methylprednisolone ester of hyaluronic acid of medium molecular weight (for the sake of simplicity, HYC141), the resulting formulation, when administered by injection into an arthrotic joint, will effectively exploit the lubricating effect of the liposomes the anti-inflammatory effect due to the pharmacological action of the cortisone derivative the viscosupplementary effect of HA and/or the derivatives thereof the protective effect of HA and/or the derivatives thereof on the integrity of the joint cartilage, mediated by the inhibitory action of IL-1, as specified above;

the effect of integration and/or substitution of the synovial fluid, altered as a result of a joint disease.

The polysaccharide modified with the cortisone derivative has an immediate action, due to its concentration outside the liposome structures, and a delaying action, due to its progressive release from the liposomes once they have been degraded. The mechanical and pharmacological effect of the formulation claimed herein is therefore amplified by the long residence time of the formulation in the joint cavity, as demonstrated by the tests described above.

For this application too, therefore, a product is obtained that differs markedly from those already known, and which is particularly suitable for use in arthrosis-type joint diseases.

In view of the special features of liposomes, it is also possible to associate the formulations described herein with biologically and/or pharmacologically active substances.

To support the aforesaid and for purely descriptive purposes, we report hereafter some examples of the preparation of formulations based on HA and/or the derivatives thereof structured with/in phospholipid liposomes.

1. Preparation of a Formulation Containing Phospholipid Liposomes and Medium-molecular Weight Hyaluronic Acid Sodium Salt.

1.1 Preparation of the Liposomes

The formulation is prepared by the classic, lipid film method.

150 mg of dipalmitoylphosphatidylcholine (DPPC) are placed in a 100 ml glass flask, and solubilised in 10 ml of chloroform and briefly shaken. The organic solvent is then eliminated using a rotating evaporator set at low pressure, at a temperature ranging between 20° and 30° C., until a thin phospholipid film is obtained on the inside surface of the flask. The chloroform residue is eliminated by vacuum evaporation at room temperature for about 12 hours. The film of DPPC is then rehydrated by adding 10 ml of phosphate buffer solution (PBS) 0.2 M at pH 7.4, while vigorously shaking. The suspension obtained undergoes six freeze-thaw cycles, immersing the flask first in liquid nitrogen and then in a thermostatic bath set at 50° C. The resulting formulation is then extruded ten times through polycarbonate filters with a pore size of 200 nm.

1.2 Structuring of HA (MW 720,000 Da)

300 mg of hyaluronic acid sodium salt of fermentative origin is dissolved for 2-4 h in 15 ml of phosphate buffer solution (PBS) 0.2 M at pH 7.4 at room temperature. The hyaluronic acid solution and the suspension of phospholipids are then mixed and the resulting solution is supplemented with 5 ml of phosphate buffer solution (PBS) 0.2 M at pH 7.4, for a final concentration of 5 mg/ml in DPPC and 10 mg/ml hyaluronic acid sodium salt. The mixture is gently stirred for about 30 minutes and lastly incubated in an oven set at 50° C. for 48 hours.

A set aliquot of this mixture is frozen for 2-4 hours at a temperature of −80° and then freeze-dried for 48-72 hours. The solid specimen is reconstituted to its initial volume by adding deionised water and dissolving after briefly stirring gently.

2. Preparation of a Formulation Containing Phospholipid Liposomes and High-molecular-weight Hyaluronic Acid Sodium Salt.

2.1 Preparation of the Liposomes

The liposomes are prepared as described in point 1.1

2.2 Structuring of HA (MW 1,800,000 Da)

300 mg of hyaluronic acid sodium salt of fermentative origin is dissolved for 2-4 h in 15 ml of phosphate buffer solution (PBS) 0.2M at pH 7.4 at room temperature. The hyaluronic acid solution and the suspension of phospholipids are then mixed and the resulting solution is supplemented with 5 ml of phosphate buffer solution (PBS) 0.2M at pH 7.4, for a final concentration of 5 mg/ml DPPC and 10 mg/ml hyaluronic acid sodium salt. The mixture is gently stirred for about 30 minutes and lastly incubated in an oven set at 50° C. for 48 hours.

A set aliquot of this mixture is frozen for 2-4 hours at a temperature of −80° and then freeze-dried for 48-72 hours. The solid specimen is reconstituted to its initial volume by adding deionised water and dissolving after briefly stirring gently.

3. Preparation of a Formulation Containing Phospholipid Liposomes and a Partial Methylprednisolone Ester of Medium-molecular-weight Hyaluronic Acid Sodium Salt.

3.1 Preparation of the Liposomes

The liposomes are prepared as described in point 1.1.

3.2 Structuring of the Methylprednisolone Ester of HA 150 mg of the methylprednisolone ester of hyaluronic acid sodium salt (MW of the hyaluronic acid 720,000 Da), in which about 45% of the carboxy groups is esterified with 6α-methylprednisolone, while the remaining 55% is in the form of sodium salt is dissolved for 2-4 h in 15 ml of phosphate buffer solution (PBS) 0.2 M at pH 7.4 at room temperature. The hyaluronic acid ester solution and the suspension of phospholipids are then mixed and the resulting solution is supplemented with 5 ml of phosphate buffer solution (PBS) 0.2 M at pH 7.4, for a final concentration of 16 mM DPPC and 5 mg/ml ester of hyaluronic acid sodium salt. The mixture is gently stirred for about 30 min and lastly incubated in an oven set at 50° C. for 2 h. A set aliquot of this mixture is frozen for 2-4 hours at a temperature of −80° and then freeze-dried for 48-72 hours. The solid specimen is reconstituted to its initial volume by adding deionised water and dissolving after briefly stirring gently.

4. Preparation of a Formulation Containing Phospholipid Liposomes and a Partial Hexadecyl Amide of Medium-molecular-weight Hyaluronic Acid Sodium Salt.

4.1 Preparation of the Liposomes

The liposomes are prepared as described in point 1.1.

4.2 Structuring of the Amide Derivative of HA 120 mg of the amide of hyaluronic acid sodium salt obtained by fermentation (MW of the hyaluronic acid, 720,000 Da), in which about 3% of the carboxy groups is amidated with hexadecylamine and the remaining 97% is in the form of sodium salt, is hydrated for 2-4 hours in 15 ml of phosphate buffer solution (PBS) 0.2 M at pH 7.4 at room temperature, and the suspension thus obtained is autoclaved for 10 min a T=121° C. The solution of hyaluronic acid amide and the suspension of phospholipids are then mixed and the resulting solution is supplemented with 5 ml of phosphate buffer solution (PBS) 0.2 M at pH 7.4, for a final concentration of 16 mM DPPC and 4 mg/ml amide of hyaluronic acid sodium salt.

The mixture is gently stirred for about 30 min and lastly incubated in an oven set at 50° C. for 48 hours.

A set aliquot of this mixture is frozen for 2-4 hours at a temperature of −80° and then freeze-dried for 48-72 hours. The solid specimen is reconstituted to its initial volume by adding deionised water and dissolving after briefly stirring gently.

5. Preparation of a Formulation Containing Phospholipid Liposomes and Low-molecular-weight O-sulphatated Hyaluronic Acid Sodium Salt.

5.1 Preparation of the Liposomes

The liposomes are prepared as described in point 1.1.

5.2 Structuring of the O-sulphated Derivative of HA 300 mg of sulphatated hyaluronic acid sodium salt (MW of the hyaluronic acid, 170,000 Da), in which about 75% of the hydroxyl groups are sulphatated and the remaining 25% is unaltered in the form of hydroxyl groups, is dissolved for 2-4 hours in 15 ml phosphate buffer solution (PBS), 0.2 M at pH 7.4 at room temperature. The sulphatated hyaluronic acid solution and the suspension of phospholipids are subsequently mixed and the resulting suspension is supplemented with 5 ml of PBS 0.2 M at pH 7.4, for a final concentration of 16 mM DPPC and 10 mg/ml sulphated hyaluronic acid.

The mixture is gently shaken for about 30 min and then incubated in an oven at 50° C.

A set aliquot of the mixture is frozen for 2-4 hours at a temperature of −80° and then freeze-dried for 48-72 hours. The solid sample is reconstituted to its initial volume by adding deionised water and dissolving it by briefly shaking it gently.

The invention being thus described, it is clear that these methods can be modified in various ways. Such modifications are not to be considered as divergences from the spirit and purpose of the invention, and any modification that would appear evident to an expert in the field comes within the scope of the following claims.

The invention claimed is:

1. A method of treating osteoarthrosis comprising intra-articularly administering to a patient in need thereof an effective amount of a pharmaceutical composition comprising:
   a hyaluronic acid and/or derivitized hyaluronic acid; and
   liposomes comprising a phospholipid,
   wherein said composition contains encapsulated hyaluronic acid and hyaluronic acid forming tubular structures between liposomes, which tubular structures are encapsulated in lipid bilayers, thereby treating the osteoarthrosis.

2. The method according to claim 1, wherein the liposomes comprise dipalmitoyl phosphatidylcholine.

3. A method of skin soft tissue filling comprising:
   Administering to a patient, at the site to be filled, an effective amount of a pharmaceutical composition comprising:
   A hyaluronic acid and/or derivitized hyaluronic acid; and
   liposomes comprising a phospholipid,
   wherein said composition contains encapsulated hyaluronic acid and hyaluronic acid forming tubular structures between liposomes, which tubular structures are encapsulated in lipid bilayers, thereby filling the skin soft tissue.

4. The method according to claim 1 or 3, wherein the molecular weight of said hyaluronic acid or derivative thereof ranges between 50,000 and $3\times10^6$ Da.

5. The method according to claim 4, wherein the hyaluronic acid derivative is at least one member selected from the group consisting of a salt, an ester, an inner ester, amides, O-sulphatated derivatives, and perearboxylated derivatives.

6. The method according to claim 5, wherein said composition further comprises at least one pharmacologically and/or biologically active substance.

7. The method according to claim 4, wherein the hyaluronic acid derivative is a hexadecyl amide.

8. The method according to claim 4, wherein the hyaluronic acid derivative is a methylprednisolone ester of hyaluronic acid.

9. The method according to claim 8, wherein the hyaluronic acid is esterified to a degree of 45% with 6α-methylprednisolone.

10. The method according to claim 1 or 3, wherein the concentration of hyaluronic acid and/or of the derivative thereof ranges between 0.1 and 50 mg/ml.

11. The method according to claim 1 or 3, wherein the phospholipids are dipalmitoyl phosphatidylcholine (DPPC).

12. The method according to claim 1 or 3, wherein the concentration of phospholipid ranges between 0.1 and 50 mg/ml.

13. The method according to claim 12, wherein the concentration of phospholipid is equal to 5 mg/ml.

14. The method according to claim 1 or 3, wherein said hyaluronic acid derivative is a hexadecyl amide.

15. A method for skin soft tissue filling which comprises:
   administering to a patient, at the site to be filled, a hexadecyl amide of hyaluronic acid and phospholipid liposomes as a composition, wherein said composition contains encapsulated hexadecyl amide of hyaluronic acid forming tubular structures between liposomes, which tubular structures are encapsulated in lipid bilayers, and wherein said phospholipid is dipalmitoylphosphatidylcholine (DPPC), thereby filling the skin soft tissue.

* * * * *